United States Patent
Takenaka et al.

(10) Patent No.: US 11,480,317 B2
(45) Date of Patent: Oct. 25, 2022

(54) LIGHT SOURCE DEVICE WITH SENSOR FOR DETECTING ANOMALY IN WAVELENGTH CONVERTING MEMBER

(71) Applicant: Panasonic Intellectual Property Management Co., Ltd., Osaka (JP)

(72) Inventors: Toshiaki Takenaka, Osaka (JP); Shintaro Hayashi, Hyogo (JP); Shogo Motegi, Osaka (JP); Yudai Shibata, Hyogo (JP); Fumiya Yagi, Osaka (JP); Takeshi Abe, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/409,251

(22) Filed: Aug. 23, 2021

(65) Prior Publication Data
US 2022/0099274 A1    Mar. 31, 2022

(30) Foreign Application Priority Data
Sep. 29, 2020 (JP) .............................. JP2020-163310

(51) Int. Cl.
*F21V 9/32* (2018.01)
*F21V 9/40* (2018.01)
*F21V 7/04* (2006.01)
*F21V 5/04* (2006.01)

(52) U.S. Cl.
CPC .................. *F21V 9/40* (2018.02); *F21V 5/04* (2013.01); *F21V 7/04* (2013.01)

(58) Field of Classification Search
CPC ... F21V 5/008; F21V 9/32; F21V 9/35; F21V 13/14; F21V 23/0442; F21V 23/0457; F21V 23/005
See application file for complete search history.

(56) References Cited

U.S. PATENT DOCUMENTS

| | | | | |
|---|---|---|---|---|
| 4,699,510 A * | 10/1987 | Alguard | ................. | G01N 21/86 356/417 |
| 7,312,430 B2 * | 12/2007 | Wong | ..................... | H05B 45/00 250/239 |
| 7,482,567 B2 * | 1/2009 | Hoelen | ..................... | G01J 1/32 362/327 |
| 7,731,389 B2 * | 6/2010 | Draganov | ................. | F21K 9/00 362/230 |
| 7,950,832 B2 * | 5/2011 | Tanaka | ................... | H05B 45/22 362/803 |

(Continued)

FOREIGN PATENT DOCUMENTS

| | | |
|---|---|---|
| JP | 61-275869 A | 12/1986 |
| JP | 5888399 B2 | 3/2016 |

(Continued)

*Primary Examiner* — Ismael Negron
(74) *Attorney, Agent, or Firm* — Greenblum & Bernstein, P.L.C.

(57) ABSTRACT

A light source device includes a plurality of light sources; a condensing optical member; a fluorescent unit that converts at least a portion of the light from the light sources and condensed by the optical member into light including converted light and light from the light sources; and a sensor that detects an anomaly in the fluorescent unit, such sensor disposed within a circular area circumscribed by the light sources.

9 Claims, 4 Drawing Sheets

(56) References Cited

U.S. PATENT DOCUMENTS

| | | | | |
|---|---|---|---|---|
| 8,550,657 | B2* | 10/2013 | Quach | F21K 9/23 |
| | | | | 362/249.02 |
| 9,736,895 | B1* | 8/2017 | Dong | F21V 23/0457 |
| 10,527,236 | B2* | 1/2020 | Daniels | F21S 41/285 |
| 10,704,755 | B2* | 7/2020 | Hadrath | F21S 41/14 |
| 2006/0226336 | A1* | 10/2006 | York | G02B 6/4298 |
| | | | | 250/206 |
| 2009/0057687 | A1* | 3/2009 | Wang | F21V 23/0457 |
| | | | | 257/E33.076 |
| 2017/0289511 | A1 | 10/2017 | Usami | |
| 2017/0347437 | A1* | 11/2017 | Hager | F21V 7/0091 |
| 2019/0032907 | A1 | 1/2019 | Kuribayashi et al. | |
| 2020/0187766 | A1 | 6/2020 | Zalevsky et al. | |

FOREIGN PATENT DOCUMENTS

| | | |
|---|---|---|
| JP | 6452172 B2 | 1/2019 |
| JP | 2019-029477 A | 2/2019 |
| JP | 2020-096834 A | 6/2020 |
| WO | 2016/051537 A1 | 4/2016 |

* cited by examiner

LIGHT SOURCE DEVICE WITH SENSOR FOR DETECTING ANOMALY IN WAVELENGTH CONVERTING MEMBER

CROSS REFERENCE TO RELATED APPLICATION

This application claims the benefit of priority of Japanese Patent Application Number 2020-163310, filed on Sep. 29, 2020, the entire content of which is hereby incorporated by reference.

TECHNICAL FIELD

The present disclosure relates to a light source device.

BACKGROUND ART

Japanese Patent No. 5888399 (Patent Literature (PTL) 1) discloses a projector including a solid-state light source that emits excitation light, phosphor that converts the excitation light into fluorescence, a reflective optical system that reflects some of light emitted from the phosphor, and a detection device that detects at least one of the excitation light and the fluorescence which are reflected by the reflective optical system. The projector can determine a deterioration state of the phosphor based on a detection result obtained by the detection device.

SUMMARY

However, like the configuration of conventional light source devices as projectors, a configuration which includes a reflective optical system for extracting some of light from wavelength converting light and primary light complicates the structure.

In view of the above, the present disclosure aims to provide a light source device that can accurately detect an anomaly in a fluorescent unit with a simple configuration.

A light source device according to an aspect of the present disclosure includes: a plurality of excitation light sources that emit primary light; an optical member that condenses the primary light; a fluorescent unit that emits secondary light including the primary light and wavelength converted light, the wavelength converted light being at least some of the primary light on which wavelength conversion is performed; and a sensor that detects an anomaly in the fluorescent unit. When seen along an optical axis of the primary light emitted by the plurality of excitation light sources, the sensor circumscribes, among the plurality of excitation light sources, a first excitation light source and a second excitation light source different from the first excitation light source, and is disposed inside an imaginary circle having, as a diameter, a line segment connecting the first excitation light source and the second excitation light source.

A light source device according to the present disclosure can accurately detect an anomaly in a fluorescent unit with a simple configuration.

BRIEF DESCRIPTION OF THE DRAWINGS

The figures depict one or more implementations in accordance with the present teaching, by way of examples only, not by way of limitations. In the figures, like reference numerals refer to the same or similar elements.

DETAILED DESCRIPTION

Hereinafter, embodiments according to the present disclosure will be described with reference to the drawings. The embodiments described below each show a particular example of the present disclosure. Therefore, numerical values, shapes, materials, structural elements, the arrangement and connection of the structural elements, etc. presented in the embodiments below are mere examples and do not limit the present disclosure. Furthermore, among the structural elements in the embodiments below, those not recited in any one of the independent claims will be described as optional structural elements.

Note that the drawings are schematic diagrams, and do not necessarily provide strictly accurate illustrations. Throughout the drawings, the same reference numeral is given to the same element.

An expression, such as substantially parallel, is used in the embodiments below. The expression substantially parallel not only means that elements are perfectly parallel with each other, but also means that the elements are approximately parallel with each other, for example. In other words, the expression substantially parallel means to include a tolerance of about several percent, for example. In addition, the expression substantially parallel means parallel within a scope in which the present disclosure is capable of demonstrating advantageous effects. This also applies to other expressions using the term "substantially".

Hereinafter, a light source device according to the present disclosure will be described.

Embodiment

[Configuration of Light Source Device 1]

Figure 1:
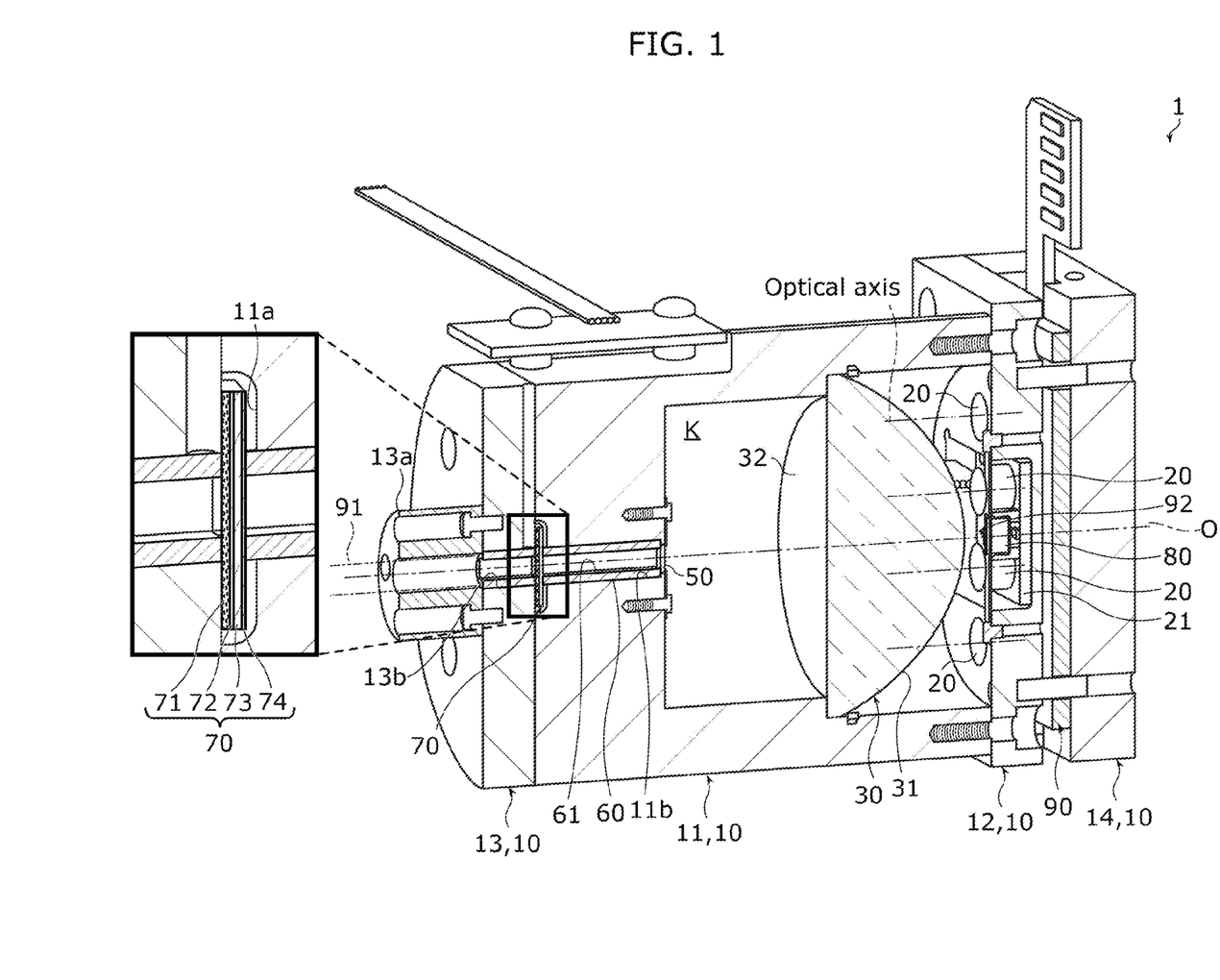
FIG. 1 illustrates a cross sectional view exemplifying a light source device according to an embodiment, and a partially enlarged cross sectional view illustrating a fluorescent unit according to the embodiment.
Figure 2:
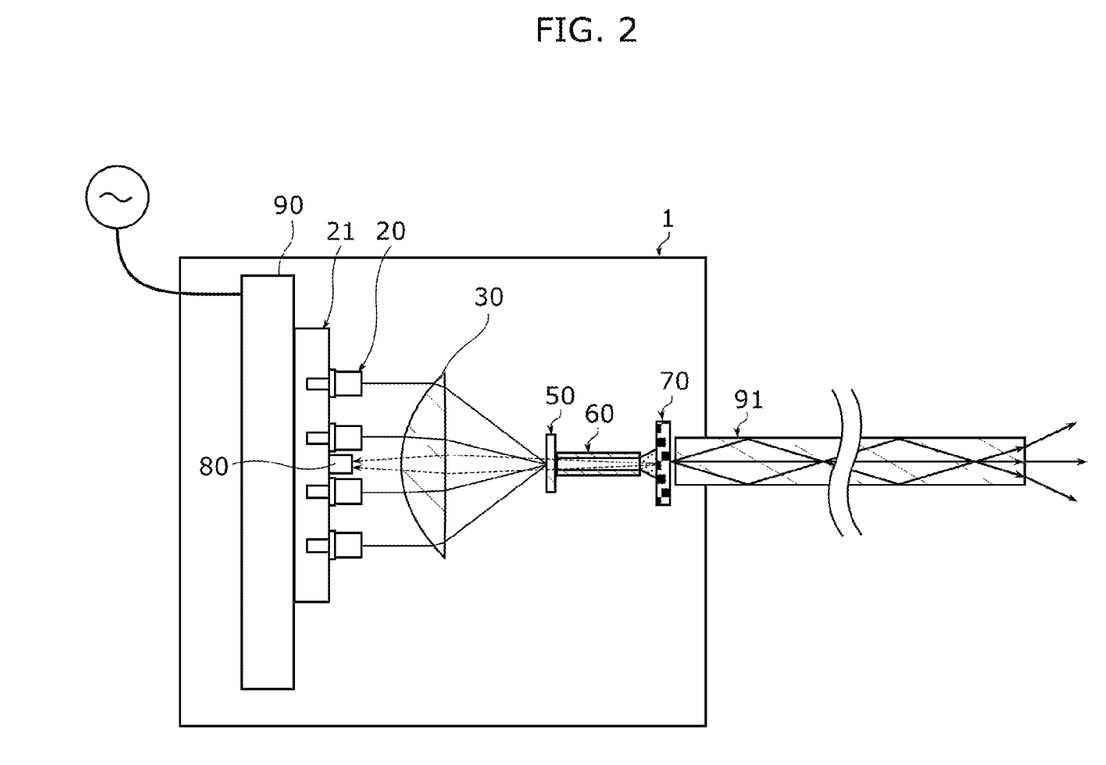
FIG. 2 is a schematic diagram exemplifying the light source device according to the embodiment.

FIG. 1 is a cross sectional view exemplifying light source device 1 according to an embodiment. FIG. 2 is a schematic diagram exemplifying light source device 1 according to the embodiment.

As illustrated in FIG. 1 and FIG. 2, light source device 1 is a lighting device that uses primary light. Light source device 1 is used in, for example, a lighting system for an endoscope, a projector, etc. Here, the primary light is excitation light, and is, for example, laser light. Note that light source device 1 may be used in a downlight, a spotlight, etc. In the embodiment, light source device 1 is connected with a connector provided in optical fiber 91 to configure a lighting system for an endoscope.

Light source device 1 emits primary light. In this embodiment, light source device 1 includes housing body 10, a plurality of excitation light sources 20, optical member 30, diffuser plate 50, light transmission body 60, fluorescent unit 70, sensor 80, filter 92, and drive circuit 90. Here, light source device 1 that uses primary light is a device in which primary light enters fluorescent unit 70 from the back face (a face on the optical member 30 side) of fluorescent unit 70, and wavelength converted light (fluorescence) on which wavelength conversion has been performed exits from the front face (a face on the optical fiber 91 side) of fluorescent unit 70.

[Housing Body 10]

Housing body 10 is an enclosure in the shape of a tube having closed ends, and extends in an anterior-posterior direction. Housing body 10 includes housing 11, support cover 12, first support 13, and second support 14.

Housing 11 is a case in the shape of a tube having one end (in a posterior direction) where opened space K is formed and the other end (in an anterior direction) which is substantially closed except for insertion hole 11b where light transmission body 60 etc. are disposed. Insertion hole 11b penetrates along the anterior-posterior direction of housing 11, and is disposed on center line O of optical member 30 which will be described later. Housing 11 accommodates, inside space K, optical member 30, diffuser plate 50, light transmission body 60, and fluorescent unit 70. In addition, recess 11a in which fluorescent unit 70 is disposed is formed on the first support 13 side (the other end) of housing 11. Recess 11a is connected to insertion hole 11b, and is formed on center line O of optical member 30. Note that housing 11 functions as a heat dissipation member for dissipating heat produced in excitation light sources 20 and fluorescent unit 70.

Support cover 12 supports excitation light sources 20 and sensor 80 such that excitation light sources 20 and sensor 80 are located opposite optical member 30. In addition, support cover 12 blocks an opening of housing 11.

First support 13 is disposed on the anterior side of housing 11, and is secured to housing 11 such that fluorescent unit 70 is interposed between first support 13 and housing 11. First support 13 includes through-hole 13b that extends from a face located opposite fluorescent unit 70. Secondary light including primary light which has diffusely transmitted through fluorescent unit 70 and wavelength converted light which is emitted by fluorescent unit 70 transmits through through-hole 13b.

First support 13 is provided with connecting terminal 13a for connecting with optical fiber 91. Connecting terminal 13a is disposed such that connecting terminal 13a and through-hole 13b overlap, and allows secondary light that has passed through through-hole 13b to pass through. Optical fiber 91 includes a light-guiding member, a connector that is mechanically connected with connecting terminal 13a of first support 13, a ferrule, etc. The light-guiding member is a transmission body having a dual structure in which a core having a high refractive index is surrounded with a clad layer having a refractive index lower than that of the core. For example, the light-guiding member includes a material, such as silica glass and plastic. The light-guiding member transmits secondary light, or in other words, wavelength converted light and primary light, which is emitted by wavelength converting member 71. The ferrule is an aligning component that holds the light-guiding member in an orientation facing fluorescent unit 70. The ferrule is inserted into the connector of optical fiber 91 when the connector of optical fiber 91 is connected to connecting terminal 13a. Accordingly, the light-guiding member and fluorescent unit 70 are disposed facing each other.

Second support 14 is disposed on the back face side of first support 13 such that driving circuit 90 is interposed between second support 14 and first support 13. Second support 14 is disposed so as to cover driving circuit 90 to protect driving circuit 90. Second support 14 is coupled to first support 13 with a fixing member such as a screw to be secured to housing 11.

In addition, each of support cover 12 and first support 13 is coupled to housing 11 with a fixing member such as a screw to be secured to housing 11. In this way, housing 11 is interposed between support cover 12 and first support 13.

[Excitation Light Source 20]

Each of excitation light sources 20 includes a semiconductor light-emitting element lens, and emits a substantially collimated primary light. Excitation light sources 20 are attached to substrate 21 such that the optical axis of primary light emitted by each excitation light source 20 is substantially parallel to one another. Excitation light sources 20 are disposed on the same surface of substrate 21, along with sensor 80. In other words, excitation light sources 20 and sensor 80 are disposed on the optical member 30 side of substrate 21.

Excitation light sources 20 are disposed such that light is caused to enter optical member 30 from first face 31. Excitation light sources 20 emit primary light toward optical member 30 to cause the primary light to enter fluorescent unit 70 from the back face of fluorescent unit 70 via optical member 30 etc. Specifically, excitation light sources 20 and substrate 21 are secured to support cover 12 such that the optical axis of primary light intersects with first face 31 of optical member 30. In addition, excitation light sources 20 are thermally connected to support cover 12 via substrate 21. The optical axis of primary light is an optical axis of primary light emitted by excitation light sources 20, and is substantially parallel to the anterior-posterior direction.

Note that although eight excitation light sources 20 are used in the embodiment, at least seven and at most nine excitation light sources 20 may be used. In addition, four excitation light sources 20 may be used in the embodiment. In this embodiment, four excitation light sources 20 are disposed in two columns, which totals eight excitation light sources 20. In this embodiment, primary light emitted by excitation light sources 20 has a predetermined wavelength within a wavelength band of from purple light to blue light.

In addition, although eight excitation light sources 20 are used as a single set of excitation light sources 20 in this embodiment, a plurality of sets of excitation light sources 20 may be used. In this case, optical member 30 is provided per set of excitation light sources 20.

Although excitation light sources 20 each are a semiconductor laser which is, for example, an InGaN-based laser diode, each excitation light source 20 may be a semiconductor laser or a light emitting diode (LED) that emits light in a wavelength band other than the wavelength band of from purple light to blue light, so long as primary light emitted can excite wavelength converting member 71 of fluorescent unit 70.

Note that an output of primary light emitted by excitation light sources 20 is controlled by driving circuit 90. In addition, excitation light sources 20 may emit, as primary light, laser light that does not excite fluorescent unit 70.

[Optical Member 30]

Optical member 30 is a light-transmissive convex lens. Optical member 30 condenses primary light emitted from excitation light sources 20, and causes the primary light to enter fluorescent unit 70 from the back face of fluorescent unit 70 via diffuser plate 50 etc. Optical member 30 condenses light which travels back toward excitation light sources 20, and causes condensed wavelength converted light and condensed primary light to be incident on sensor 80 via optical member 30. Here, the light which travels back toward excitation light sources 20 includes wavelength converted light and primary light which travel toward excitation light sources 20, but also includes, for example, reflected light reflected inside light source device 1, scattered light scattered inside light source device 1, wavelength converted light which is primary light on which wavelength conversion has been performed by wavelength converting member 71 of fluorescent unit 70, etc. That is, the light which travels back toward excitation light sources 20 is some of the reflected light, some of the scattered light, and some of the wavelength converted light.

Optical member 30 is disposed inside housing 11 such that optical member 30 intersects with the optical axis of primary light emitted by excitation light sources 20. Specifically, optical member 30 is disposed inside housing 11 such that primary light emitted by excitation light sources 20 directly enters optical member 30. In other words, optical member 30 is disposed inside housing 11 such that the optical axis of primary light emitted by excitation light sources 20 is substantially parallel to center line O of optical member 30. Center line O of optical member 30 runs through the center of optical member 30, and is a segment line (the principal axis) substantially perpendicular to first face 31 and second face 32 of optical member 30.

Optical member 30 includes first face 31 and second face 32. Optical member 30 is a convex lens whose first face 31 is a curved face and whose second face 32 is a plane face. First face 31 is a face which is located opposite excitation light sources 20 and through which primary light emitted by excitation light sources 20 directly enters. Second face 32 is a face opposite first face 31 (a face located opposite diffuser plate 50) from which primary light that has entered from first face 31 and transmitted through the inside of optical member 30 exits. In this embodiment, first face 31 has a face in the shape of a hemisphere.

Note that optical member 30 in this embodiment is a convex lens, but is not limited to a convex lens so long as optical member 30 is an optical device capable of condensing primary light and causing the primary light to enter an end face of optical fiber 91. For example, optical member 30 may be a prism, a concave mirror, a diffraction grating, etc.

[Diffuser Plate 50]

Diffuser plate 50 is disposed between light transmission body 60 and optical member 30, and is disposed so as to intersect with center line O of optical member 30. Specifically, diffuser plate 50 overlaps light transmission body 60, and is disposed so as to block an end portion of housing 11 and an opening on the posterior side of light transmission body 60. Diffuser plate 50 is an optical member in the shape of a plate which diffuses primary light condensed by optical member 30, and allows the primary light to transmit through.

Diffuser plate 50 includes an entrance face through which primary light enters, and an exit face opposite the entrance face from which the primary light that has been diffused by diffuser plate 50 and transmitted through diffuser plate 50 exits. The entrance face of diffuser plate 50 is located opposite optical member 30, and is substantially orthogonal to center line O of optical member 30. The exit face of diffuser plate 50 is located opposite light transmission body 60, and is substantially orthogonal to center line O of optical member 30.

From the viewpoint of laser resistance, diffuser plate 50 in this embodiment includes an inorganic material, or particularly, inorganic glass. Note that diffuser plate 50 may include, for example, a light-transmissive material, such as acrylic and polycarbonate.

From the viewpoint of laser resistance, diffuser plate 50 has a glass surface on which diffusion processing is performed to display light diffusion characteristics in this embodiment. Alternatively, diffuser plate 50 may have a transparent panel whose surface is finely textured (embossments and microprisms) by imparting, to the surface, surface treatment such as emboss processing or laser machining, or may have a transparent panel on which a dot pattern is printed or etched to display light diffusion characteristics. Furthermore, an anti-reflective (AR) coating may be applied on the entrance face and the exit face of diffuser plate 50 for the purpose of reducing loss of light. From the viewpoint of laser resistance, it is desirable that the AR coating is an inorganic film. In addition, it is desirable that the AR coating is a multilayer film from the viewpoint of transmittance, but the AR coating may be an inexpensive single layer film. Note that diffuser plate 50 may be a translucent diffuser plate in which a light dispersing agent (light scattering material) is dispersed inside glass.

In this embodiment, the exit face of diffuser plate 50 has better light diffusion characteristics than the entrance face to diffuse primary light that has transmitted through diffuser plate 50, for example. Note that the exit face may have better light diffusion characteristics than the entrance face, or both the exit face and the entrance face may have good light diffusion characteristics.

[Light Transmission Body 60]

Light transmission body 60 is a light pipe or a beam homogenizer which includes glass as a base material, and has an inner surface that is coated with a dielectric multilayer so as to efficiently reflect primary light. When light transmission body 60 is cut across a plane orthogonal to the lengthwise direction of light transmission body 60, the outer perimeter of a cross section of light transmission body 60 is in the shape of a polygon. In this embodiment, the outer perimeter of the cross section is in the shape of a square. In this case, four pieces of glass plates are joined together to configure light transmission body 60.

Note that light transmission body 60 may be a metal light pipe having the inner surface to which a coating that efficiently reflects a laser wavelength is applied. Note that light transmission body 60 may be a glass rod including a light-transmissive material such as glass.

Light transmission body 60 is accommodated inside housing 11. Light transmission body 60 is disposed in a state in which light transmission body 60 is inserted into insertion hole 11b which extends across from the end portion inside housing 11 to a face on the first support 13 side to be supported by housing 11. Light transmission body 60 is disposed inside housing 11 such that the central axis of light transmission body 60 substantially matches with the above-described center line O. Light transmission body 60 is disposed, inside housing 11, such that light transmission body 60 is interposed between diffuser plate 50 and wavelength converting member 71.

In addition, light transmission body 60 includes transmission path 61 through which primary light diffused by diffuser plate 50 transmits. Light transmission body 60 emits primary light that has passed through transmission path 61. When transmission path 61 is cut across a plane orthogonal to a direction in which primary light is transmitted, the outer perimeter of a cross section of transmission path 61 included in light transmission body 60 is in the shape of a polygon. Since primary light that is guided through the inside of light transmission body 60 repeatedly reflects inside light transmission body 60 while being transmitted through the inside of light transmission body 60 when transmission path 61 included in light transmission body 60 is in the shape of a polygon, the primary light transmitted through the inside of light transmission body 60 is readily mixed. Since primary light transmits through transmission path 61 while being mixed, light transmission body 60 can emit mixed primary light (tophat primary light) toward fluorescent unit 70.

Transmission path 61 is a space from an opening on the posterior side of light transmission body 60 to an opening of the anterior side of light transmission body 60, and allows primary light to pass through. The opening on the posterior side of light transmission body 60 is an opening located opposite the exit face of diffuser plate 50, and is covered by diffuser plate 50. The opening on the anterior side of light transmission body 60 is an opening located opposite fluorescent unit 70, and is covered by fluorescent unit 70.

[Fluorescent Unit 70]

Fluorescent unit 70 is phosphor (optical member) which converts primary light mixed by light transmission body 60 into wavelength converted light. Fluorescent unit 70 emits secondary light including primary light and wavelength converted light which is at least some of the primary light on which wavelength conversion is performed. Specifically, fluorescent unit 70 in the shape of a plate emits the wavelength converted light, while diffusing primary light condensed by optical member 30 and allowing the primary light to transmit through.

Fluorescent unit 70 performs wavelength conversion on primary light that has entered from the back face of fluorescent unit 70, and emits the primary light on which the wavelength conversion is performed from the front face of fluorescent unit 70. More specifically, primary light that has transmitted through light transmission body 60 enters fluorescent unit 70 from the back face of fluorescent unit 70. In this embodiment, the intensity distribution of light that enters fluorescent unit 70 from the back face of fluorescent unit 70 is uniform, and is substantially uniform on an illumination face illuminated by primary light. Fluorescent unit 70 performs wavelength conversion on primary light that has entered from the back face of fluorescent unit 70, and emits the primary light on which the wavelength conversion is performed from the front face of fluorescent unit 70.

Fluorescent unit 70 is disposed between housing 11 and first support 13 in a state in which fluorescent unit 70 is in contact with housing 11 and first support 13. Fluorescent unit 70 is disposed between light transmission body 60 and first support 13, and is disposed in and secured to recess 11a formed in housing 11 so as to intersect with center line O of optical member 30. In other words, fluorescent unit 70 is disposed so as to overlap light transmission body 60 and to block the opening on the anterior side of light transmission body 60.

Fluorescent unit 70 is a flat plate. In this embodiment, fluorescent unit 70 includes, for example, anti-reflective (AR) layer 74, light transmitter 73, reflective film 72, and wavelength converting member 71 (phosphor layer). Fluorescent unit 70 has a multilayered structure in which AR layer 74, light transmitter 73, reflective film 72, and wavelength converting member 71 are stacked in the stated order.

AR layer 74 is stacked on the back face (a face on the light transmission body 60 side) of light transmitter 73. AR layer 74 allows primary light to effectively transmit through toward light transmitter 73, thereby improving light efficiency.

Light transmitter 73 is a light-transmissive substrate, and includes sapphire, for example. Note that a sapphire substrate having high thermal conductivity is used for light transmitter 73, but light transmitter 73 is not limited to the sapphire substrate. Instead of the sapphire substrate, a transparent substrate such as glass may be used as light transmitter 73.

Reflective film 72 is stacked on a face of wavelength converting member 71 through which primary light enters. Reflective film 72 is a dichroic mirror, such as a dielectric multilayer including $FMg$, $SiO_2$, $TiO_2$, etc. For example, reflective film 72 allows primary light in a wavelength band of from blue light to purple light to transmit through, and reflects light in wavelength bands other than the wavelength band of from blue light to purple light. Reflective film 72 is stacked on the front face (a face on the first support 13 side) of light transmitter 73. Reflective film 72 allows the primary light to efficiently transmit through, and reflects wavelength converted light.

In addition, although reflective film 72 is provided for causing wavelength converted light to travel toward optical fiber 91, or in other words, is provided for improving the optical extraction efficiency of the wavelength converted light, reflective film 72 may allow light in a particular wavelength band to travel back toward excitation light sources 20. For example, reflective film 72 may allow light in a wavelength band of red light, blue light, etc. to travel back toward excitation light sources 20.

Wavelength converting member 71 includes phosphor that emits wavelength converted light that is at least some of primary light on which wavelength conversion is performed. The phosphor is dispersed and kept in a binder which is a transparent material including, for example, ceramic such as glass or silicon resin. Wavelength converting member 71 is, for example, an yttrium aluminum garnet (YAG)-based phosphor, a CASN-based phosphor, an SCASN-based phosphor, or a barium (Ba), aluminum (Al), magnesium (Mg) (BAM)-based phosphor. The type of phosphor can be selected as appropriate according to a type of primary light. Note that the binder is not limited to ceramic or silicon resin. The binder may include other transparent materials such as transparent glass, etc.

Wavelength converting member 71 emits secondary light including primary light and wavelength converted light which is at least some of the primary light on which wavelength conversion is performed. Specifically, wavelength converting member 71 emits secondary light including primary light and wavelength converted light by (i) emitting wavelength converted light, which is some of primary light transmitted through light transmission body 60 on which wavelength conversion is performed by wavelength converting member 71, and (ii) allowing the rest of the primary light on which wavelength conversion is not performed to diffusely pass through wavelength converting member 71.

In addition, wavelength converting member 71 may be, for example, a red phosphor, a green phosphor, a blue phosphor, etc., and may emit wavelength converted light, such as red light, green light, and blue light, according to primary light. In this case, these wavelength converted lights of red light, green light, and blue light may be combined to produce white light.

In this embodiment, wavelength converting member 71 emits quasi-white wavelength converted light produced by combining (i) green to yellow wavelength converted light produced by wavelength converting member 71 absorbing some of blue primary light emitted from excitation light sources 20, and (ii) the blue primary light exited from wavelength converting member 71 without being absorbed by wavelength converting member 71. Note that in the case where excitation light sources 20 emit blue primary light, wavelength converting member 71 may include several types of phosphors which absorb some of the blue primary light and convert the some of blue primary light into green to yellow wavelength converted light.

Note that wavelength converting member 71 has thermal quenching characteristics that display a decrease in wavelength conversion efficiency when temperature rises. Since a loss involved in wavelength conversion turns into heat, it is important to ensure heat dissipation of wavelength converting member 71. Accordingly, it is desirable that fluorescent unit 70 is in contact with each of housing 11 and first support 13 for readily dissipating heat produced in wavelength converting member 71 via the sapphire substrate, etc.

[Sensor 80]

Sensor 80 detects an anomaly in wavelength converting member 71 of fluorescent unit 70. Specifically, sensor 80 detects an anomaly in wavelength converting member 71 of fluorescent unit 70 from light which travels back toward excitation light sources 20. Although the light which travels back toward excitation light sources 20 includes primary light and wavelength converted light, sensor 80 detects condensed wavelength converted light and condensed primary light which are condensed by optical member 30. Here, an anomaly in wavelength converting member 71 is, for example, damage to fluorescent unit 70, a leak of primary light, and a failure to provide fluorescent unit 70 in housing 11. Sensor 80 outputs, to a control device, information indicating light which has traveled back toward excitation light sources 20 and has been detected.

The control device determines an anomaly in wavelength converting member 71, namely, fluorescent unit 70, based on the information obtained from sensor 80 which indicates light which has traveled back toward excitation light sources 20. For example, when the control device determines the presence of an anomaly in fluorescent unit 70 based on the information indicating light which has traveled back toward excitation light sources 20, the control device may deactivate excitation light sources 20, or may notify those around light source device 1 of the information indicating the presence of an anomaly in fluorescent unit 70. For example, the control device may stop electric power supplied to excitation light sources 20 by controlling a drive controller. In addition, when the control device determines the absence of an anomaly in fluorescent unit 70 based on the information indicating light which has traveled back toward excitation light sources 20, the control device need not provide a notification, or may notify those around light source device 1 of information indicating that fluorescent unit 70 is normal. As described above, the control device can monitor the state of fluorescent unit 70 of light source device 1.

Next, a location of sensor 80 relative to excitation light sources 20 will be described.

Figure 3:
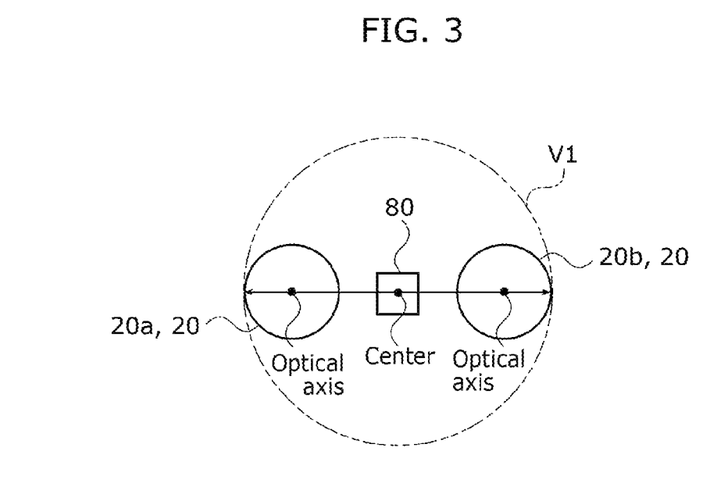
FIG. 3 is a diagram exemplifying an imaginary circle having, as a diameter, a line segment connecting a first excitation light source and a second excitation light source, and a sensor disposed inside the imaginary circle.

FIG. 3 is a diagram exemplifying imaginary circle V1 having, as a diameter, a line segment indicated by an arrow which connects first excitation light source 20a and second excitation light source 20b, and a sensor disposed inside imaginary circle V1. In this embodiment, imaginary circle V1 is a perfect circle, but imaginary circle V1 may be an ellipse. As illustrated in FIG. 3, when seen along the optical axis of primary light emitted by excitation light sources 20, sensor 80 circumscribes, among the plurality of excitation light sources 20, first excitation light source 20a and second excitation light source 20b different from first excitation light source 20a, and is disposed inside imaginary circle V1 having, as a diameter, a line segment connecting first excitation light source 20a and second excitation light source 20b. First excitation light source 20a and second excitation light source 20b are two adjacent excitation light sources 20 among the plurality of excitation light sources 20. In this embodiment, sensor 80 is interposed between first excitation light source 20a and second excitation light source 20b.

In addition, the following describes a location of sensor 80 in the case where eight excitation light sources 20 are disposed as exemplified in the embodiment.

Figure 4:
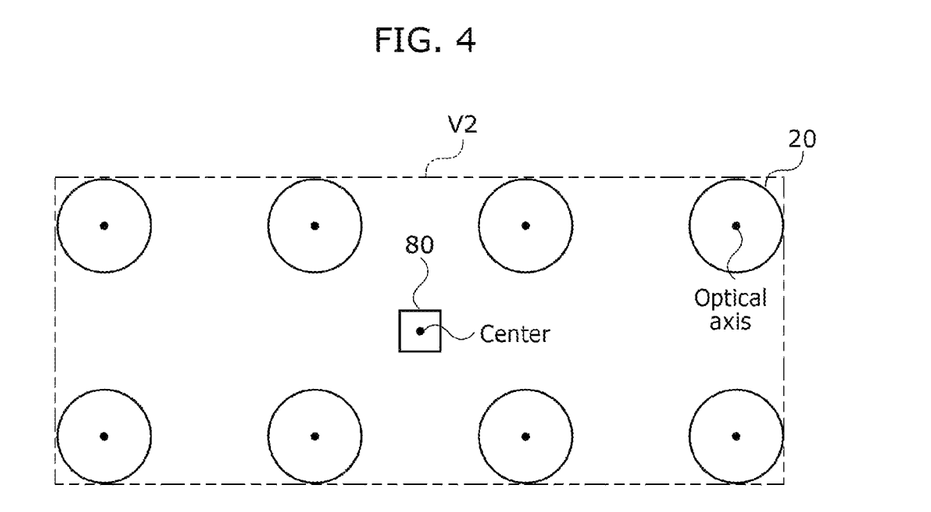
FIG. 4 is a diagram exemplifying the sensor disposed at a location overlapping an approximate center of an approximate quadrilateral shape, in the case where an outer perimeter collectively defined by eight excitation light sources has the approximate quadrilateral shape.

FIG. 4 is a diagram exemplifying sensor 80 disposed at a location overlapping an approximate center of an approximately quadrilateral shape, in the case where an outer perimeter collectively defined by eight excitation light sources 20 has the approximate quadrilateral shape. In FIG. 4, the outer perimeter collectively defined by the eight excitation light sources 20 is indicated by chain double-dashed line V2. When the eight excitation light sources 20 are seen along the optical axis of primary light emitted by excitation light sources 20, sensor 80 is disposed inside the outer perimeter collectively defined by the plurality of excitation light sources 20 disposed. In this embodiment, sensor 80 is disposed at a location overlapping the center of the outer perimeter collectively defined by the plurality of excitation light sources 20 disposed. In this case, sensor 80 is disposed on center line O of optical member 30. Moreover, as illustrated in FIG. 1, the light-receiving surface of sensor 80 is disposed on support cover 12 such that the light-receiving surface of sensor 80 is located opposite first face 31 of optical member 30 via filter 92.

Figure 5:
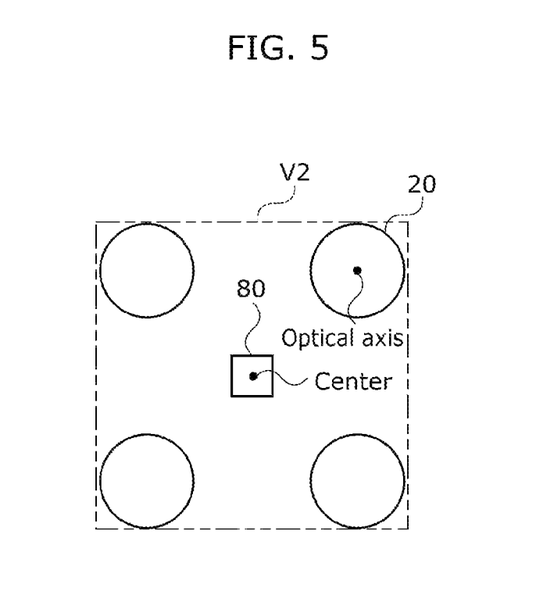
FIG. 5 is a diagram exemplifying the sensor disposed at a location overlapping an approximate center of an approximate quadrilateral shape, in the case where an outer perimeter collectively defined by four excitation light sources has the approximate quadrilateral shape.

Alternatively, four excitation light sources 20 may be disposed as illustrated in FIG. 5, for example. FIG. 5 is a diagram exemplifying sensor 80 disposed at a location overlapping an approximate center of an approximate quadrilateral shape, in the case where an outer perimeter collectively defined by four excitation light sources 20 has the approximate quadrilateral shape. In FIG. 5, the outer perimeter collectively defined by the four excitation light sources 20 is indicated by chain double-dashed line V2. When the four excitation light sources 20 are seen along the optical axis of primary light emitted by excitation light sources 20, sensor 80 may be disposed at a location overlapping the center of the outer perimeter collectively defined by the plurality of excitation light sources 20 disposed.

Figure 6:
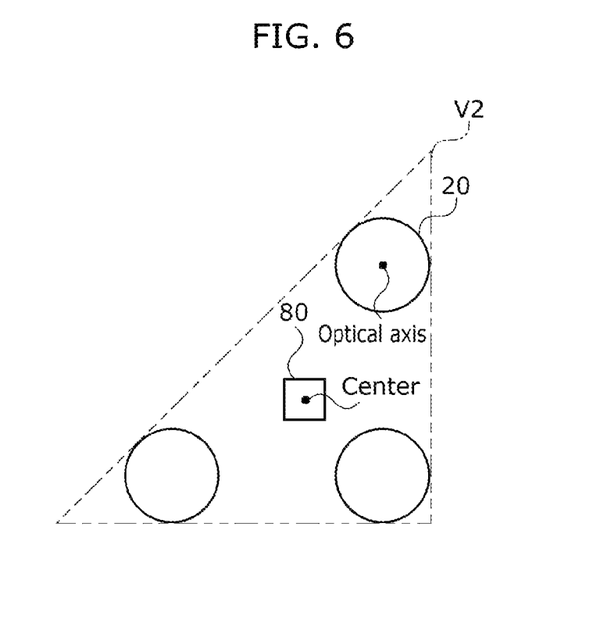
FIG. 6 is a diagram exemplifying the sensor disposed at a location overlapping an approximate center of an approximate triangle shape, in the case where an outer perimeter collectively defined by three excitation light sources has the approximate triangle shape.

Furthermore, three excitation light sources 20 may be disposed as illustrated in FIG. 6, for example. FIG. 6 is a diagram exemplifying sensor 80 disposed at a location overlapping an approximate center of an approximate triangle shape, in the case where an outer perimeter collectively defined by three excitation light sources 20 has the approximate triangle shape. In FIG. 6, the outer perimeter collectively defined by the three excitation light sources 20 is indicated by chain double-dashed line V2. When the three excitation light sources 20 are seen along the optical axis of primary light emitted by excitation light sources 20, sensor 80 may be disposed at a location overlapping the center of the outer perimeter collectively defined by the plurality of excitation light sources 20 disposed.

Sensor 80 includes a photodiode, and a light receiving element of an image sensor etc. which is capable of receiving a signal. An amplifier circuit for receiving an analog signal by the light receiving element, and a circuit for converting the received analog signal into a digital signal may be connected to sensor 80.

[Filter 92]

Filter 92 is disposed on the optical member 30 side of sensor 80, and blocks light in a predetermine wavelength band. Specifically, filter 92 is a photoselective pigment absorbing-type colored glass, a notch filter, etc. which filters light incident on the light-receiving surface of sensor 80, or in other words, wavelength converted light and primary light which travel back toward excitation light sources 20. Filter 92 is interposed between sensor 80 and optical member 30, and covers the light-receiving surface of sensor 80. Filter 92 may block light in a wavelength band of blue light by absorbing the light in the wavelength band of blue light, or may block light in wavelength bands other than the wavelength band of blue light by absorbing the light in wavelength bands other than the wavelength band of blue light. This makes it possible to block light other than light in a wavelength band which sensor 80 is expected to detect. Accordingly, an S/N ratio for sensor 80 to detect an anomaly in wavelength converting member 71 can be improved. Note that although filter 92 is provided in the embodiment, filter 92 is not an essential structural element for light source device 1, and thus is not necessarily provided in light source device 1.

[Drive Circuit 90]

Drive circuit 90 is electrically connected with an electric power system via an electric power line etc. Drive circuit 90 supplies electric power to each of excitation light sources 20 and sensor 80. In addition, each excitation light source 20 outputs light under the control of drive circuit 90 such that each excitation light source 20 emits primary light.

Drive circuit 90 may have a function of dimming primary light emitted by each excitation light source 20. In addition, drive circuit 90 may include, for example, an oscillator that drives each excitation light source 20 based on a pulse signal.

[Other Configurations]

Light source device 1 may be connected to a lighting device for emitting, as illumination light, secondary light transmitted via optical fiber 91. The lighting device may include, for example, a stainless-steel fiber coupling, a glass lens, an aluminum holder, and an aluminum enclosure.

Specific Example of Light Source Device 1

Light source device 1 according to the embodiment uses eight excitation light sources 20 each of which includes a collimator lens. The eight excitation light sources 20 are packaged as a single set, and secured to support cover 12. The eight excitation light sources 20 are disposed at an attachment pitch of 11 mm. Primary light emitted by excitation light sources 20 has a wavelength of 455 nm and an output of 6 W to 20 W. Optical member 30 is an aspherical lens including a plane face (second face 32) and a convex face (first face 31). Optical member 30 has the focal length of 50 mm, the diameter of 50 mm, the curvature of 21, and the thickness of 21 mm. Optical member 30 includes crown glass as a material. Optical member 30 includes first face 31 on which an AR coating for a wavelength of 455 nm is applied. Optical member 30 includes second face 32 on which an AR coating for a wavelength of 550 nm is applied. In addition, diffuser plate 50 is made of Pyrex (registered trademark) glass having uneven surface to diffuse primary light. The haze value of diffuser plate 50 is 50%. Diffuser plate 50 includes two faces on each of which an AR coating for a wavelength of from 440 nm to 650 nm is applied. Furthermore, light transmission body 60 is a hollow beam homogenizer in which four pieces of glass plates on each of which a visible light reflective coating is applied are joined together. Moreover, fluorescent unit 70 includes a dichroic mirror, a sapphire substrate on which an AR coating is applied, wavelength converting member 71, etc. Wavelength converting member 71 is an YAG phosphor or a multicolor phosphor containing ZnO, etc. The dichroic mirror is configured to reflect wavelength converted light toward the anterior direction, but allows about 3% of entire light having wavelength of 550 nm to transmit in the posterior direction for wavelength converted light to travel back toward sensor 80. Sensor 80 includes a photodiode (ROHM BH1603FVC), and a filter (HOYA yellow long path filter) in front of the photodiode. Sensor 80 is disposed in the center of the eight excitation light sources 20 which are packaged as a single set. Sensor 80 includes a variable resistor for gain control on a substrate on which the photodiode is attached.

[Operation]

In such light source device 1, primary light emitted from each excitation light source 20 enters optical member 30 from first face 31, transmits through optical member 30, and exits from second face 32. The condensed primary light enters diffuser plate 50 from the entrance face of diffuser plate 50. The primary light that has entered diffuser plate 50 from the entrance face of diffuser plate 50 diffusely exits from the exit face of diffuser plate 50 by transmitting through diffuser plate 50. The primary light then transmits through transmission path 61 of light transmission body 60, and enters fluorescent unit 70. Some of the primary light that has entered fluorescent unit 70 is absorbed by wavelength converting member 71 and exits from fluorescent unit 70 as wavelength converted light, and the rest of the primary light transmits through fluorescent unit 70, without wavelength conversion being performed. The wavelength converted light and the primary light which have exited from fluorescent unit 70 enter the light-guiding member of optical fiber 91, are guided through optical fiber 91 to a distal end portion of optical fiber 91, and exit from the distal end portion. The light exited from the distal end portion can illuminate a predetermined location.

Advantageous Effects

Next, advantageous effects of light source device 1 according to the embodiment will be described.

As has been described above, light source device 1 according to the embodiment includes: a plurality of excitation light sources 20 that emit primary light; optical member 30 that condenses the primary light; fluorescent unit 70 that emits secondary light including the primary light and wavelength converted light which is at least some of the primary light on which wavelength conversion is performed; and sensor 80 that detects an anomaly in fluorescent unit 70. In addition, when seen along an optical axis of the primary light emitted by the plurality of excitation light sources 20, sensor 80 circumscribes, among the plurality of excitation light sources 20, first excitation light source 20a and second excitation light source 20b different from first excitation light source 20a, and is disposed inside imaginary circle V1 having, as a diameter, a line segment connecting first excitation light source 20a and second excitation light source 20b.

Accordingly, some of primary light that has entered fluorescent unit 70 travels back toward excitation light sources 20, and some of the primary light on which wavelength conversion is performed also travels back toward excitation light sources 20. The disposition of sensor 80 inside imaginary circle V1 as described in the embodiment makes it possible for sensor 80 to detect light (wavelength converted light and primary light) which travels back toward excitation light sources 20.

Therefore, light source device 1 can accurately detect an anomaly in fluorescent unit 70 with a simple configuration.

Particularly, it is possible to ensure freedom in designing light source device 1, since sensor 80 can be disposed inside imaginary circle V1.

In addition, in light source device 1 according to the embodiment, sensor 80 is disposed inside an outer perimeter collectively defined by the plurality of excitation light sources 20 disposed.

With this, it is possible to dispose sensor 80 at a location in which light which travels back toward excitation light sources 20 is likely to be concentrated. Accordingly, it is expected that a great amount of light which travels back toward excitation light sources 20 to be incident on sensor 80. This further increases accuracy of sensor 80 detecting an anomaly in fluorescent unit 70. Moreover, it is possible to ensure freedom in designing light source device 1, since sensor 80 can be disposed inside the outer perimeter.

In addition, in light source device 1 according to the embodiment, sensor 80 is disposed at a location overlapping the center of the outer perimeter collectively defined by the plurality of excitation light sources 20 disposed.

With this, it is possible to dispose sensor 80 at a location in which light which travels back toward excitation light sources 20 is likely to be concentrated. Accordingly, it is expected that a great amount of light which travels back toward excitation light sources 20 to be incident on sensor 80. This further increases accuracy of sensor 80 detecting an anomaly in fluorescent unit 70.

In addition, in light source device 1 according to the embodiment, first excitation light source 20a and second excitation light source 20b are two adjacent excitation light sources 20 among the plurality of excitation light sources 20. Moreover, sensor 80 is disposed between first excitation light source 20a and second excitation light source 20b.

With this, it is possible to dispose sensor 80 at a location in which light which travels back toward excitation light sources 20 is likely to be concentrated. Accordingly, it is expected that a great amount of light which travels back toward excitation light sources 20 to be incident on sensor 80. This further increases accuracy of sensor 80 detecting an anomaly in fluorescent unit 70.

In addition, in light source device 1 according to the embodiment, the plurality of excitation light sources 20 are disposed on the same surface of substrate 21, along with sensor 80.

With this, it is possible to reliably detect light which travels back toward excitation light sources 20. In addition, the disposition of the plurality of excitation light sources 20 and sensor 80 on the same surface makes it possible to reduce enlargement of light source device 1.

In addition, in light source device 1 according to the embodiment, optical member 30 is a convex lens.

With this, light which travels back toward excitation light sources 20 is condensed and is caused to be incident on sensor 80, thereby ensuring light condensing efficiency of sensor 80. Accordingly, it is possible to increase accuracy of sensor 80 detecting an anomaly in fluorescent unit 70.

In addition, in light source device 1 according to the embodiment, sensor 80 is disposed on center line O of optical member 30.

Accordingly, the disposition of sensor 80 on center line O of optical member 30 makes it possible to readily cause light which travels back toward excitation light sources 20 to be incident on sensor 80 without the use of a convex lens having a particular shape. This can reduce an increase in cost of manufacturing optical member 30.

In addition, in light source device 1 according to the embodiment, fluorescent unit 70 includes: wavelength converting member 71 that emits wavelength converted light which is at least some of the primary light on which wavelength conversion is performed; and reflective film 72 stacked on a face of wavelength converting member 71 through which the primary light enters. Reflective film 72 allows the primary light to transmit through, and reflects the wavelength converted light.

With this, sensor 80 can accurately detect light in a predetermined wavelength band, since it is possible to cause only light in the predetermined wavelength band to travel back toward excitation light sources 20.

In addition, light source device 1 according to the embodiment further includes filter 92 that is disposed between sensor 80 and optical member 30, and blocks light in a predetermine wavelength band.

Accordingly, filter 92 can block light other than light in a wavelength band which sensor 80 is expected to detect. This can improve an S/N ratio for sensor 80 to detect an anomaly in wavelength converting member 71.

In addition, light source device 1 according to the embodiment includes: a plurality of excitation light sources 20 that emit primary light; optical member 30 that condenses the primary light; fluorescent unit 70 through which the primary light condensed by optical member 30 enters and which emits secondary light including the primary light and wavelength converted light which is at least some of the primary light on which wavelength conversion is performed; and sensor 80 that detects an anomaly in fluorescent unit 70. Sensor 80 detects light which travels back from the fluorescent unit 70 side toward the plurality of excitation light sources 20 via optical member 30, and outputs information indicating the light detected to a control device. When seen along an optical axis of the primary light emitted by the plurality of excitation light sources 20, sensor 80 circumscribes, among the plurality of excitation light sources 20, first excitation light source 20a and second excitation light source 20b different from first excitation light source 20a, and is disposed inside imaginary circle V1 having, as a diameter, a line segment connecting first excitation light source 20a and second excitation light source 20b.

Variations, Etc.

The present disclosure has been described as above based on the embodiment, but the present disclosure is not limited thereto.

In addition, a light source device according to the embodiment may use a fluorescent unit not including a dichroic mirror. In this case, a filter that covers the light-receiving surface of a sensor may be provided.

The present disclosure also encompasses: embodiments achieved by applying various modifications conceivable to those skilled in the art to each of embodiments and variations; and embodiments achieved by optionally combining the structural elements and the functions of each embodiment and variation without departing from the essence of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

The invention claimed is:

1. A light source device, comprising:
a plurality of excitation light sources that emit primary light;
an optical member that condenses the primary light;
a fluorescent device that converts at least a portion of the primary light condensed by the optical member, and emits secondary light including primary light and wavelength converted light;
a sensor that detects an anomaly in the fluorescent device; and
a filter disposed between the sensor and the optical member that blocks light in a predetermined wavelength band;
wherein when seen along an optical axis of the primary light emitted by the plurality of excitation light sources, the sensor is disposed inside an imaginary circle having a diameter defined as a line segment connecting a first excitation light source among the plurality of excitation light sources and a second excitation light source among the plurality of excitation light sources.

2. The light source device according to claim 1,
wherein the sensor is disposed between the first excitation light source and the second excitation light source.

3. The light source device according to claim 1, further comprising:
a substrate,
wherein the plurality of excitation light sources and the sensor are disposed on a first surface of the substrate.

4. The light source device according to claim 1,
wherein the optical member is a convex lens.

5. The light source device according to claim 1,
wherein the sensor is disposed on a center line of the optical member.

6. The light source device according to claim 1,
wherein the fluorescent device includes
a wavelength converting member; and
a reflective film provided on a face of the wavelength converting member through which the primary light enters, the reflective film conducting the primary light and reflecting the wavelength converted light.

7. The light source device according to claim 1,
wherein the sensor is disposed inside an outer perimeter collectively defined by the plurality of excitation light sources.

8. The light source device according to claim 7,
wherein the sensor is disposed at a location overlapping a center of the outer perimeter collectively defined by the plurality of excitation light sources.

9. A light source device, comprising:
a plurality of excitation light sources that emit primary light;
an optical member that condenses the primary light;
a fluorescent device through which the primary light condensed by the optical member enters and which emits secondary light including the primary light and wavelength converted light, the wavelength converted light being at least some of the primary light on which wavelength conversion is performed;
a control device; and
a sensor that detects an anomaly in the fluorescent device, by detecting light travelling back from the fluorescent device to the plurality of excitation light sources via the optical member, the sensor outputting a signal indicating the detected light to the control devices; and
a filter disposed between the sensor and the optical member that blocks light in a predetermined wavelength band,
wherein, when seen along an optical axis of the primary light emitted by the plurality of excitation light sources, the sensor is disposed inside an imaginary circle having a diameter defined as a line segment connecting a first excitation light source among a plurality of excitation light sources and a second excitation light source among the plurality of excitation light sources.

* * * * *